United States Patent [19]

Bentz et al.

[11] Patent Number: 4,971,952
[45] Date of Patent: Nov. 20, 1990

[54] METHOD OF TREATING INFLAMMATION WITH CARTILAGE INDUCING FACTOR

[75] Inventors: Hanne Bentz, Newark; Larry Ellingsworth, San Jose; Rosa Armstrong, Palo Alto, all of Calif.

[73] Assignee: Collagen Corporation, Palo Alto, Calif.

[21] Appl. No.: 263,635

[22] Filed: Oct. 27, 1988

Related U.S. Application Data

[63] Continuation-in-part of Ser. No. 836,672, Mar. 6, 1986, Pat. No. 4,806,523, which is a continuation-in-part of Ser. No. 763,337, Aug. 6, 1985, abandoned.

[51] Int. Cl.$^5$ .............. A61K 37/02; C07K 7/10
[52] U.S. Cl. ............................... 514/12; 514/2; 530/324
[58] Field of Search ............ 424/95; 514/2, 21, 12, 514/801, 886, 887, 825; 530/356, 840, 324

[56] References Cited

U.S. PATENT DOCUMENTS 4,473,551 9/1984 Schinitsky .................. 424/95

FOREIGN PATENT DOCUMENTS 0128849 12/1984 European Pat. Off. .
0169016 1/1986 European Pat. Off. .

OTHER PUBLICATIONS

Shipley et al., (1985) Proc. Natl. Acad. Sci. USA 82:4147–4151.
Moses, (1985) Fed. Proc. 44(3), VIII abstract.
Kehrl et al., (1985) Clinical Research 33(2):610A.
Brinckerhoff, (1983) Arthritis and Rheumatism 26(11):1370–1379.
Tashjian et al., (1985) Proc. Natl. Acad. Sci. USA 82:4545–4538.
Roberts et al., (1985) Proc. Natl. Acad. Sci. USA 82:119–123.
Baserga, (1981) Handbook of Experimental Pharmacology 57:385–404.

*Primary Examiner*—Jacqueline Stone
*Attorney, Agent, or Firm*—Irella & Manella

[57] ABSTRACT

Inflammation, acute and/or chronic, is treated with a CIF (TGF-beta). The CIF may be administered locally or systemically, depending upon the indication, and does not require coadministration of activator or cofactor for efficacy.

8 Claims, 3 Drawing Sheets

```
Ala Leu Asp Thr Asn Tyr Cys Phe Ser Ser Thr Glu Lys Asn
Cys Cys Val Arg Gln Leu Tyr Ile Asp Phe Arg Lys Asp Leu
Gly Trp Lys Trp Ile His Glu Pro Lys Gly Tyr His Ala Asn
Phe Cys Leu Gly Pro Cys Pro Tyr Ile Trp Ser Leu Asp Thr
Gln Tyr Ser Lys Val Leu Ala Leu Tyr Asn Gln His Asn Pro
Gly Ala Ser Ala Ala Pro Cys Cys Val Pro Gln Ala Leu Glu
Pro Leu Pro Ile Val Tyr Tyr Val Gly Arg Lys Pro Lys Val
Glu Gln Leu Ser Asn Met Ile Val Arg Ser Cys Lys Cys Ser
```

FIG.1

METHOD OF TREATING INFLAMMATION WITH CARTILAGE INDUCING FACTOR

CROSS-REFERENCE TO RELATED APPLICATIONS

This application is a continuation-in-part of copending U.S. patent application Ser. No. 836,672 filed 6 Mar. 1986, now U.S. Pat. No. 4,806,523, which is a continuation-in-part of U.S. patent application Ser. No. 763,337, filed 6 Aug. 1985, now abandoned.

DESCRIPTION

1. Technical Field

This invention is in the field of anti-inflammatory compounds. More particularly it relates to using polypeptides called cartilage-inducing factors (CIFs) and functionally related polypeptides as factors for inhibiting inflammatory processes involving lymphohistiocytic inflammation, granulomatous inflammation, and acute inflammation.

2. Background

Commonly owned copending U.S. patent application Ser. No. 630,938, filed 16 July 1984, now abandoned, describes two bovine bone-derived CIFs, designated CIF-A and CIF-B. Both have molecular weights of approximately 26,000 daltons by SDS-PAGE and are dimers. They each exhibit in vitro chondrogenic activity by themselves, as measured by cartilage specific proteoglycan (PG) production in an agarose gel culture model using fetal rat mesenchymal cells. Neither, however, is chondrogenically active in vivo by itself. Amino acid sequencing of the CIF-A showed that it has a partial (30 amino acids) N-terminal sequence identical to that reported for a human placenta-derived polypeptide called beta-type transforming growth factor (TGF-beta). The partial N-terminal sequence of CIF-B is different from that of TGF-beta. Both CIFs exhibit activity in the TGF-beta assay (ability to induce anchorage-independent growth of normal rat kidney cell colonies in soft agar).

TGF-beta derived from bovine kidney, human placenta, and human platelets is described in International Patent Application No. PCT/US83/01460, published 29 Mar. 1984 under No. WO84/01106, EPA 84450016.5, published 19 Dec. 1984 under No. 0128849, and U.S. patent application Ser. Nos. 500,832, 500,833, and 500,927, filed 3 June 1983 all abandoned. These applications present data showing that such TGF-beta, when combined with EGF or TGF-alpha, (1) promotes cell proliferation in the above mentioned soft agar culture assay and (2) promotes cell proliferation and protein deposition in a rat soft tissue wound healing model. The applications characterize the TGF-betas as being dimers having a molecular weight of approximately 26,000 daltons by SDS-PAGE.

DISCLOSURE OF THE INVENTION

The present invention is based on the finding that the two bone-derived CIFs described above exhibit anti-inflammatory activity. Evaluations of implants containing CIF indicate that CIF is active both locally and systemically for inhibiting acute and/or chronic inflammation. Based on the similarity (or perhaps identity in the case of CIF-A) of these polypeptides to TGF-betas, it is believed that TGF-betas also have these newly discovered activities. These activities appear to be independent of the presence of activating agents or cofactors and are distinct from the in vitro chondrogenic activity and cell proliferation activity reported previously. For convenience, the term CIF is used in this section and the claims as a generic term to encompass CIF-A, CIF-B, the TGF-betas and functional equivalents thereof.

A subsequent finding that CIF is localized at sites of hematopoiesis and lymphopoiesis suggests that CIF may also be efficacious in treating dysfunction or malfunction of red blood cell and/or lymphocyte development.

Accordingly, the invention provides several new therapeutic methods:

A principal aspect of the invention is a method of treating inflammation in a patient comprising administering an anti-inflammatorily effective amount of a CIF to the patient. Both acute and chronic forms of inflammation may be so treated. Further the treatment may be systemic or CIF may be administered locally to treat predetermined sites of inflammation. The method of the invention is effective inter alia for treating inflammation mediated by granulocytes and/or lymphocytes, thus effecting either systemic or local immunosuppression.

Another aspect of the invention is a method of treating a patient for an indication associated with dysfunction or malfunction of hematopoiesis or lymphopoiesis comprising administering an effective amount of a CIF to the patient.

BRIEF DESCRIPTION OF THE DRAWINGS

In the drawings:

FIG. 1 is the amino acid sequence of platelet-derived human TGF-beta monomer.

FIG. 5 shows the results of CIF-A or CyA on hematologic parameters when injected subcutaneously, as described in Example 8.

FIG. 6 presents additional results from Example 8.

FIG. 7 presents additional results from Example 8.

MODES FOR CARRYING OUT THE INVENTION

Figure 2:
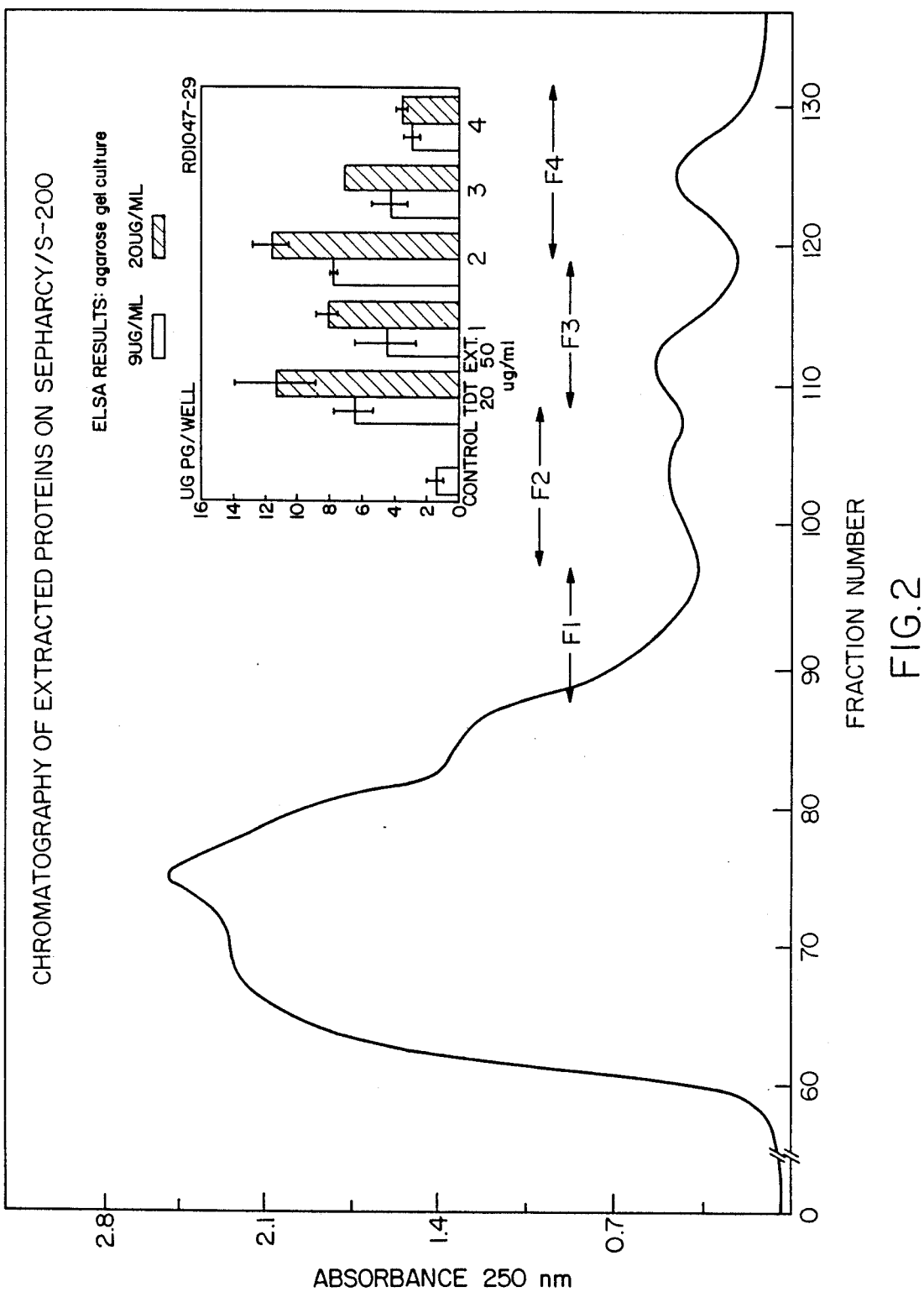
FIG. 2 is a graph of the optical densities (absorbances) (280 nm) of the gel filtration fractions of the example 1 ( ¶ C)
Figure 3:
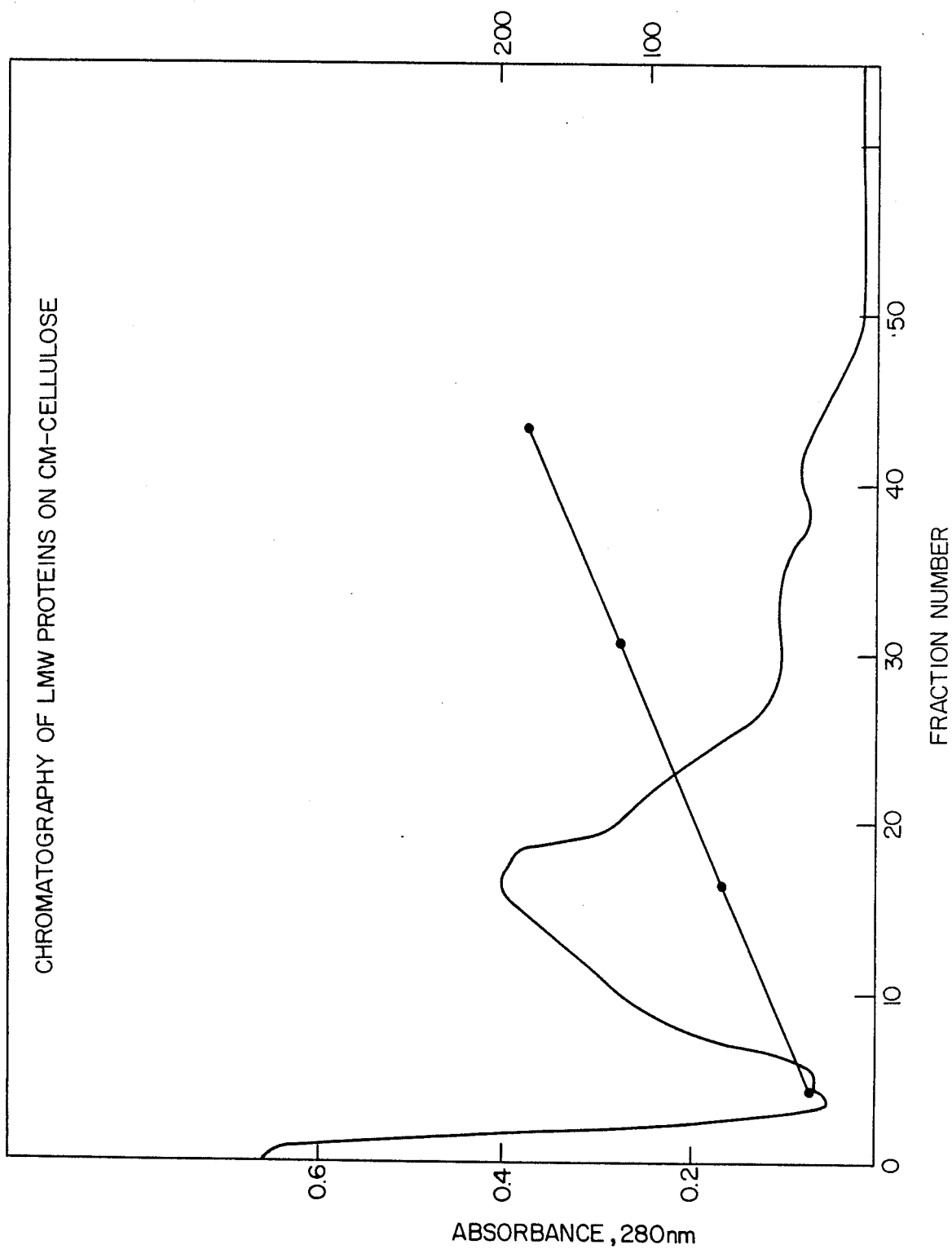
FIG. 3 is a graph of the optical densities (280 nm) of eluate fractions from the preparative ion exchange chromatography of the example 1 ( ¶ D)

As used herein the term "inflammation" is intended to encompass both acute responses (i.e., a response in which the inflammatory processes are active) and chronic responses (i.e., a response marked by slow progress and formation of new connective tissue). Chronic and acute inflammation may be distinguished by the cell types involved. Acute inflammation often involves polymorphonuclear neutrophils; whereas chronic inflammation is normally characterized by a lymphohistiocytic and/or granulomatous response. Examples of specific types of inflammation are diffuse inflammation, focal inflammation, croupous inflammation, interstitial inflammation, obliterative inflammation, parenchymatous inflammation, reactive inflammation, specific inflammation, toxic inflammation, immunosuppression, and traumatic inflammation.

As used herein the term "treat" is intended to mean prophylaxis or attenuation of an existing condition. Accordingly, in the case of inflammation, the invention method may be used to prevent inflammation (for example, to prevent transplant rejection) or alleviate existing inflammation.

The term "functional equivalent" as used to describe a polypeptide is intended to mean polypeptides, whether native or synthetic and regardless of species or derivation, that have the same amino acid sequence as the referenced polypeptide, and polypeptides of substantially homologous (i.e., at least 90% identity in amino acid sequence) but different amino acid sequence, which difference(s) does not affect inflammatory activity adversely.

CIF-A, CIF-B and TGF-betas exhibit activity in the TGF-beta assay described in *Methods for Preparation of Media, Supplements, and Substrate for Serum-Free Animal Cell Culture* (1984) pp 181–194, Alan R. Liss, Inc. That assay determines ability to induce anchorage-independent growth in non-neoplastic normal rat kidney (NRK) fibroblasts by measuring the formation of cell colonies in soft agar. Procedures for obtaining TGF-betas from platelets, placenta and kidney tissues are described in International patent publication WO84/01106 and EPA publication No. 0128849. Briefly, they involve extracting the source material with acid-ethanol, sizing the extract by gel filtration, and isolating the TGF-beta from the filtrate by high performance liquid chromatography (HPLC).

A procedure for isolating CIFs from bovine bone is described in commonly owned, copending U.S. application Ser. No. 630,938, filed 16 July 1984. It involves extracting demineralized bone (DMB) with an extractant (e.g., $\geq$4M guanidine hydrochloride, 8M urea) that solubilizes nonfibrous proteins, gel filtering the extract to obtain a < 30 Kd fraction, chromatographing the fraction on carboxymethyl cellulose (CMC) at pH 4.5–5.5, preferably 4.8, eluting the CMC-adsorbed fraction with an NaCl gradient, and purifying the proteins from the portion eluting at about 150–250 mM NaCl by RP-HPLC or gel electrophoresis.

CIF-A, CIF-B, and the TGF-betas isolated to date from natural sources are polypeptide dimers of approximately 25 to 26 Kd molecular weight as determined by SDS-PAGE. Nature (1985) 316:701–705 reports a cDNA nucleotide sequence and deduced amino acid sequence for platelet-derived human TGF-beta. Mature platelet-derived human TGF-beta is characterized as a homodimer of a 112 amino acid-long monomer.

Platelet/placenta/kidney-derived TGF-beta and CIF-A and CIF-B are non-species specific as regards TGF-beta activity. It is believed, therefore, that these polypeptides have been highly conserved among animal species (i.e., a given polypeptide from different mammalian species has an amino acid sequence that varies, if at all, in one or more amino acid residue additives, deletions, or substitutions that do not affect the non-species specific activity of the molecule adversely) and have cross-species functionality. Accordingly, CIF-A, CIF-B, and the TGF-betas may be derived from cells or tissue of diverse animal origin or may be obtained by recombinant DNA technology. Correlatively, CIF (TGF-beta) from one vertebrate species may be used to treat another vertebrate species. The most common usage of CIF (TGF-beta) as an anti-inflammatory agent will be in the treatment of humans, domestic animals such as cattle, sheep, and pigs, and sports or pet animals such as dogs, cats, and horses. CIF-A and CIF-B are preferred for use in the invention method.

EXAMPLES

The following examples are intended to illustrate specific embodiments of the invention. They are not intended to limit the invention in any manner.

EXAMPLE 1

(Preparation of CIFs from Bone)

A. Preparation of Demineralized Bone

Bovine metatarsal bone was obtained fresh from the slaughterhouse and transported on dry ice. The bones were cleaned of marrow and non-bone tissues, broken in fragments smaller than 1 cm diameter, and pulverized in a mill at 4° C. The pulverized bone was washed twice with 9.4 liters of double distilled water per kg of bone for about 15 min each, and then washed overnight in 0.01 N HCl at 4° C. Washed bone was defatted using 3×3 volumes ethanol, followed by 3×3 volumes diethylether, each washed for 20 min. and all at room temperature. The resulting defatted bone powder was then demineralized in 0.5 N HCl (25 l/kg defatted bone) at 4° C. The acid was decanted and the resulting DMB washed until the wash pH was greater than 4, and the DMB dried on a suction filter.

B. Extraction of Noncollagenous Proteins

The DMB as prepared in ¶ A was extracted with 3.3 l of 4 M guanidine-HCl, 10 mM ethylenediaminetetraacetic acid (EDTA), pH 6.8, 1 mM PMSF, 10 mM NEM per kg for 16 hr, the suspension suction filtered and the non-soluble material extracted again for 4 hr. The soluble fractions were combined and concentrated at least 5-fold by ultrafiltration using an Amicon ultrafiltration (10K) unit, and the concentrate dialyzed against 6 changes of 35 volumes cold deionized water over a period of 4 days, and then lyophilized. All of the procedures of this paragraph were conducted at 4° C. except the lyophilization which was conducted under standard lyophilization conditions.

C. Gel Filtration

The extract from ¶ B, redissolved in 4 M guanidine-HCl, was fractionated on a Sephacryl ® S-200 column equilibrated in 4 M guanidine-HCl, 0.02% sodium azide, 10 mM EDTA, pH 6.8. Fractions were assayed by their absorbance at 280 nm and the fractions were combined as shown in FIG. 1. Fraction F2 of FIG. 1, constituting a low molecular weight (LMW, 10,000–30,000 daltons) protein fraction was dialyzed against 6 changes of 180 volumes of deionized water and lyophilized. All operations except lyophilization and dialysis (4° C.) were conducted at room temperature.

D. Ion Exchange Chromatography

Fraction F2 from ¶ C was dissolved in 6 M urea 10 mM NaCl, 1 mM NEM, 50 mM sodium acetate, pH 4.8 and centrifuged at 10,000 rpm for 5 min. The supernatant was fractionated on a CM52 (a commercially available CMC) column equilibrated in the same buffer. Bound proteins were eluted from the column using a 10 mM to 400 mM NaCl gradient in the same buffer, and a total volume of 350 ml at a flow rate of 27 ml/hr. Three major fractions, designated CM-1, CM-2 and CM-3, were collected as shown in FIG. 2. CM-2 and CM-3 eluted at approximately 150–250 mM NaCl. Each fraction was dialyzed against 6 changes of 110 volumes of deionized water for 4 days and lyophilized. All of the foregoing operations were conducted at room temperature except dialysis (4° C.).

E. RP-HPLC

The combined lyophilized fractions CM-2 and CM-3 from D were each dissolved in 0.1% trifluoroacetic acid (TFA) and aliquots of the solutions loaded onto a Vydac C18 RP-HPLC columns (4.6 mm ID×25 cm) and washed with 0.1% TFA for 5 min at 1 ml/min. The eluting solvent was a 0%–60% acetonitrile gradient in 0.1% TFA at a rate of 2%/min.

Two peaks were obtained from the RP-HPLC of combined CM-2 and CM-3: peak A at about 29.5 min and peak B at about 31.2 min. The proteins of these peaks are the subject of said U.S. patent application Ser. No. 630,938. They are designated CIF-A and CIF-B, respectively.

The proteins were stored in 0.1% TFA/acetonitrile eluting solution at −20° C. until used.

F. Characterization of CIF-A and CIF-B

Table 1 below gives the partial amino acid compositions of CIF-A and CIF-B.

TABLE 1

| Amino Acid | Amt (mols/100 mols recovered) | |
|---|---|---|
| | CIF-A | CIF-B |
| Asp | 9.2 | 12.0 |
| Glu | 9.2 | 8.5 |
| Ser | 7.0 | 10.6 |
| His | 2.7 | 0.9 |
| Gly | 16.5 | 22.0 |
| Thr | 2.7 | 0.0 |
| Arg | 5.9 | 4.3 |
| Ala | 6.6 | 6.7 |
| Tyr | 3.2 | 1.9 |
| Met | 0.0 | 0.0 |
| Val | 7.5 | 2.4 |
| Phe | 3.0 | 3.0 |
| Ile | 3.9 | 2.2 |
| Leu | 8.6 | 8.2 |
| Lys | 13.9 | 17.3 |
| Pro | ND | ND |
| Cys | ND | ND |
| Trp | ND | ND |

SDS-PAGE analysis of CIF-A and CIF-B indicate that both have a molecular weight of approximately 26,000 daltons. Both proteins exhibited activity in the TGF-beta assay referred to above comparable to that reported for TGF-betas derived from human platelets, human placenta, or bovine kidney.

N-terminal amino acid sequencing of the first 30 amino acids of CIF-A and CIF-B was carried out and found to be as follows:

CIF-A 1           5                    10
Ala—Leu—Asp—Thr—Asn—Tyr—Cys—Phe—Ser—Ser—Thr—Glu—Lys—

15                  20                    25
Asn—Cys—Cys—Val—Arg—Gln—Leu—Tyr—Ile—Asp—Phe—Arg—Lys—

30
Asp—Leu—Gly—Trp—.

CIF-B 1           5                    10
Ala—Leu—Asp—Ala—Ala—Tyr—Cys—Phe—Arg—Asn—Val—Gln—Asp—

15                  20                    25
Asn—(Cys—Cys)—Leu—Arg—Pro—Leu—Tyr—Ile—Asp—Phe—Lys—Arg—

30
Asp—Leu—Gly—Trp—.

The N-terminal amino acid sequence of CIF-A is identical to that reported for platelet-derived human TGF-beta (see Nature, infra).

EXAMPLE 2

(Anti-Inflammatory Activity of CIFs)

A. Formulation of CIF-A/CIF-B-Containing Implants

A collagenous carrier was prepared by mixing collagen in solution (CIS, 1–3 mg protein/ml; sold by Collagen Corporation under the trademark VITROGEN 100 ®) with bone collagen powder (BCP, lyophilized solids from bone collagen) to give a minimal final concentration of 10% collagen from CIS. A 2:1 weight ratio mixture of CIF-A and CIF-B (in 0.1% TFA) was added to carrier in weight ratios of 1:1200, 1:4500, 1:6000, 1:8000, and 1:20000. The formulations were stirred for 1–2 hr at 4° C. and either directly lyophilized or dialyzed against water and lyophilized. Carrier alone was used as a comparative control.

B. Histoloqical Evaluation of Implant Formulations Implantation:

The lyophilized formulations were rehydrated with two parts by weight of cold sterile water and mixed to form a homogeneous paste. The rehydrated material was formed into compact pellets (80–100 mg wet weight). The pellets were implanted subcutaneously in the ventral thoracic region of young male rats. Each rat received bilateral implants. The explants were recovered at 3, 10, and 14 days post implantation and evaluated histologically.

Histological Evaluation:

Explants were fixed in 10% neutral formalin and paraffin embedded by routine methods. Sections were subsequently stained with either hematoxylineosin or with Gomori trichrome.

Results:

The results of the histological evaluations are summarized below.

3-Days Post Implantation:

Carrier alone.

At three days post implantation, the implant was, for the most part, acellular. Sparse neutrophils were the most apparent cell type.

CIF-Carrier.

The implant was also relatively acellular at three days. However, there was an apparent activation of fibroblasts from adjacent muscle and the surrounding subcutaneous tissues. These fibroblasts contained abundant cytoplasm and were, for the most part, euchromatic suggesting the cells were highly activated. Fibroblast infiltration was beginning at the margins of the implant.

10 Days Post Implantation:

Carrier alone.

The inflammatory profile was markedly changed by 10 days following implantation. The implant contained a diffuse mixed inflammatory cell infiltrate dominated by lymphocytes and histiocytes. Focal areas of granulocytes (neutrophils and eosinophils) and giant cells were evident around some of the bone collagen particles.

CIF-Carrier.

There were few inflammatory cells associated with the implant at this time point. Numerous hyperplastic fibroblasts were present throughout the implant. A collagenous connective tissue matrix was evident around and surrounding the bone collagen powder particles.

14 Days Post Implantation:

Carrier alone.

By 14 days post implantation, most bone collagen particles were sequestered by granulomas consisting of lymphocytes, histiocytes and giant cells. Implant-associated fibrosis was evident as well as multifocal areas of eosinophils.

CIF-Carrier.

Implant-associated inflammation was negligible compared with the control implants. A dense collagenous connective tissue matrix was evident throughout the implant. Morphologically, the fibroblasts appeared to be metabolically less active than at earlier time points.

These histological observations demonstrate that CIF inhibits inflammatory cell function in vivo. The lack of polymorphonuclear neutrophils, lymphocytes, and histiocytes at the CIF-containing implant sites indicates that CIF may function as a potent anti-inflammatory agent.

In the implants having CIF to carrier weight ratios of 1:8000 and 1:20000 there was a marked reduction in implant-associated inflammation compared with carrier alone implants. The implants containing higher CIF to carrier weight ratios developed a dense collagenous connective tissue matrix throughout the implant. At all CIF levels, implant-associated inflammation was negligible compared to no CIF.

In similar in vivo studies in which the rats received bilateral implants with and without CIF containing extracts, it was noted that inflammation was reduced or absent in the implant remote from the CIF containing implant. These observations indicate that CIF acts systemically as well as locally.

When used as a local anti-inflammatory agent the CIF (and/or TGF-beta) will usually be formulated in effective amounts with pharmaceutically acceptable carriers in weight ratios to carrier in the range of 1:1000 to 1:20000. If tissue deposition at the site is not desired, the level of CIF to carrier may be lowered to below that (e.g., at weight ratios below about 1:6000 in the case of collagen carrier) which promotes tissue deposition. In addition to being formulated as an injectable, the CIF may be incorporated (dispersed) into solid permeable implants such as collagenous soft and hard tissue implants, prostheses, sponges, wound dressings and sutures to modulate local inflammatory responses to such solid bodies. Since such implants are made from permeable materials the CIF can diffuse from the implant and exert its anti-inflammatory properties. If it is desired to minimize other activities of CIF (cell proliferation, tissue deposition) the CIF will be incorporated free of activating agents or cofactor, preferably at levels below that which promote tissue deposition.

When used to treat inflammation at internal body sites locally, the CIF- or TGF-beta-containing formulation is injected, inhaled, placed surgically, or otherwise administered locally, depending on the particular formulation, and the site where inflammation control is desired.

For systemic administration CIF may be formulated with conventional carriers used with water-soluble proteins for injection into circulation. Alternatively, it may be formulated as a sustained release implant formulation if the indication being treated requires.

The amount of CIF (TGF-beta) administered to treat inflammation will depend upon the patient, the inflammatory condition being treated, and the mode of administration. In general, the amounts administered to adult humans will be in the range of about 0.1 to 1000 ug. When CIF is administered locally, amounts in the lower portion of this range will normally be used, typically 0.1 to 10 ug. Correspondingly, systemic administration will typically involve amounts in the 10-1000 ug range.

CIF may be particularly effective in the treatment of inflammation involving the respiratory system. In this application, the CIFs may be administered by inhalation with a suitable aerosol. In this form, these factors would be useful for the treatment of diffuse interstitial diseases of the lung such as asbestosis, silicosis, or coal-miner's pneumoconiosis; the treatment of immunological diseases that involve the respiratory tract such as rheumatoid arthritis, lupus erythematosus, or Goodpasture's syndrome; and the treatment of granulomatous inflammation of the lungs and pulmonary tract such as Wegener's granulomatosus and eosinophilic granulomatosus.

These anti-inflammatory peptides may be combined with carriers in the form of a salve, ointment, or other topical formulation and thereby by useful in the control of dermal inflammation by topical application. Such formulations would be particularly useful in the local treatment of psoriasis vulgaris, contact dermatitis, dermal ulcers, and acute or chronic eczematous dermatitis.

CIF may be either used alone or combined with a slow release carrier and injected into or around joints, bone, or muscle for the control of inflammation associated with various diseases. Some examples include myositis (viral, bacterial, parasitic, fungal or autoimmune processes), myasthenia gravis, osteomyelitis, osteoarthritis and rheumatoid arthritis.

Since the CIF molecules have been shown to be stable at low pH and resistant to enzyme digestion, these factors may be delivered systemically by ingestion. These properties make these factors particularly useful for controlling inflammation in the gastrointestinal tract. This would be particularly useful for the treatment of gastric and duodenal ulcers, granulomatous gastritis, esophagitis (numerous causes), enteristis (numerous causes), and colitis (numerous causes).

EXAMPLE 3

(Hematopoietic Modulation by CIF-A)

A. Synthetic Polypeptide Synthesis

A synthetic polypeptide, referred to as A1/30, was constructed to be identical to the N-terminal amino acid sequence (residues 1-30) of CIF-A (TGF-beta). The peptide A1/30 was synthesized by a solid-phase method. The peptide was assembled on p-methylbenzhydrylamine resin, cleaved from the resin, deprotected via a 2-step hydrogen fluoride procedure, and purified by reverse-phase liquid chromatography on octadecylsilica. Peptide A1/30 was determined to be homogeneous by RP-HPLC and thin layer chromatography and the amino acid sequence was verified by gas-phase sequence analysis.

B. Radioiodination

Purified CIF-A and CIF-B were radioiodinated with Na$^{125}$I (Amersham, Chicago, Ill.) using a lactoperoxidase method. The specific activity was 0.8 to $1.0 \times 10^7$ cpm/ug protein.

C. Immunization

A New Zealand white rabbit was immunized with peptide A1/30 at multiple intramuscular sites biweekly for 6-10 weeks using 250 to 500 ug of peptide A1/30 per injection. The primary immunization was in Freund's complete adjuvant and the subsequent boosts were in Freund's incomplete adjuvant. Ten days following the final boost, the rabbit was bled by cardiac puncture. The blood was clotted at 22° C. for 4 hr and overnight at 4° C., and the serum was collected and stored at −70° C.

D. Antibody Purification

Serum IgG was purified using Sepharose ® protein-A. Briefly, serum was diluted with an equal volume of 0.01 M Tris (pH 7.2) containing 0.15 M NaCl. Antibodies were precipitated with an equal volume of saturated ammonium sulfate adjusted to pH 8.0 (4° C.) and collected by centrifugation at $100,000 \times g$ (30 min). The protein pellet was resuspended in a minimal volume of pH 7.2 PBS and dialyzed against PBS. The retentate was clarified by centrifugation and the supernatant applied to a 10 ml column of Sepharose ® protein-A. Bound IgG was eluted with 0.1 M glycine-HCl (pH 2.0). The antibodies were immediately neutralized (4.0 M Tris), dialyzed against PBS, and lyophilized.

E. Enzyme-Linked Immunosorbent Assay (ELISA)

Antiserum was evaluated for reactivity with peptide A1/30, CIF-A, or the low molecular weight bone extract by an ELISA. Peptide A1/30 was solubilized in PBS, while purified CIF-A or the partially purified bone extracts were solubilized in 0.01 N HCl. Antigens were diluted in 0.01 M carbonate buffer (pH 9.6) and 400 ng of protein in 100 ul volume were added to the wells of a microtiter plate. Peptides A1/30 and CIF-A were air dried onto the wells overnight. Plates containing the partially purified extract were sealed and stored overnight at 4° C. Prior to use, nonspecific protein binding to the ELISA plate was blocked by incubating with PBS containing 1% (w/v) BSA for 1 hr. Antiserum was serially twofold diluted and 100 ul were added to each well for 1 hr. The plates were washed with PBS containing 0.05% (v/v) Tween ®-20 and 1% (w/v) BSA, and peroxidase-conjugated goat F(ab')$_2$ anti-rabbit IgG was added for 2 hr. The plates were washed 5-8 times and the peroxidase substrate was added. The substrate consisted of 2,2'-azino-di-(3-ethylbenzthiazoline) sulfonic acid (ABTS, 0.03% w/v) and 0.03% (v/v) H$_2$O$_2$ in 0.1 M citrate buffer (pH 4.0). Color was allowed to develop for 30 min and the optical density determined at 414 nm.

F. Antibody Competition ELISA

An antibody competition ELISA was used to determine if antibodies detected by the ELISA were antigen specific. Various concentrations (1 to 100 ng) of soluble competing antigen peptide (A1/30) were added to the wells to compete the binding of antibody to plastic adsorbed synthetic polypeptide: for these studies the antiserum was diluted 1:5000 and the antibodies were washed away and the bound antibodies detected by the ELISA.

G. Sodium Dodecyl Sulfate—Polyacrylamide Gel Electrophoresis

Purified and partially purified proteins were separated by SDS-PAGE. The stacking gels were 4% and the separating gels were 15% polyacrylamide. The gels were either silver stained or electrophoretically transferred to nitrocellulose. In some instances, the gels were "spiked" with $^{125}$I-labeled CIF-A as an internal standard to identify CIF-A in the gel or the protein to blot.

H. Two-Dimensional Acetic Acid-Urea PAGE

Partially purified low molecular weight bone extracts were evaluated by two-dimensional polyacrylamide gel electrophoresis. Proteins (20 to 40 ug) were separated (by mass and charge) in the first dimension in 15% polyacrylamide containing 2.5 M urea and acetic acid in glass tubes ($2 \times 4 \times 125$ mm) for 5-6 hr at 160 V (constant voltage), and the second dimension in a 15% SDS-polyacrylamide slab gel. The gels were either silver stained or the proteins were transferred to nitrocellulose (below). In some instances, the gels were "spiked" with $^{125}$I-labeled CIF-A and CIF-B and subsequently autoradiographed to identify the factors on the silver stained gel.

I. Immunoblotting

Samples were first electrophoretically separated in one or two dimensions. After separation, the proteins were transferred to nitrocellulose using a trans blot apparatus filled with 25 mM Tris (pH 8.3) and 192 mM glycine (pH 8.3) containing 20% (v/v) methanol. The proteins were transferred for 18 hr at 170 mA (constant current). Following transfer, non-specific protein binding was blocked with PBS buffer containing 0.05% (v/v) Tween ®-20 and 1% (w/v) BSA for 1-2 hr. The protein blots were then incubated for 2 hr in a 1:100 dilutions of rabbit anti-A1/30 serum. The blot was washed for 30 min with the same buffer and then incubated for 1 hr with 200,000 cpm/ml [$^{125}$I] protein-A. The immunoblots were washed, air dried, and autoradiographed with Kodak XAR-5 film at −80° C. for 1 to 18 hr.

J. Immunohistochemical Staining

The cell association and distribution of CIF-A was determined by immunohistochemical staining methods. Fetal bovine tissues were collected from a single animal at 6 months gestation. The tissues were fixed in 10% neutral formalin. Hard tissues were demineralized in 10% formic acid. The tissues were dehydrated and paraffin embedded with a Fisher Histomatic Tissue Processor model 166A (15 hr cycle). The sections were deparaffinized with xylene and endogenous peroxidase blocked with 0.1% hydrogen peroxide in 0.01 M Tris containing 0.15 M NaCl (15 min). The sections were then treated with 1 mg/ml testicular hyaluronidase in 0.1 M sodium acetate (pH 5.5) in saline (30 min at 37°

C.). Nonspecific protein binding was blocked with 0.5% (w/v) BSA in Tris-saline (15 min). The sections were incubated with optimally diluted (1:50) rabbit (IgG) anti-A1/30 or nonimmune rabbit IgG for 1 hr, washed with Tris-saline, and incubated for 1 hr with peroxidase conjugated goat F(ab')$_2$ anti-rabbit IgG. The slides were treated with diaminobenzidine substrate buffer. The substrate buffer consisted of 0.5 mg/ml diaminobenzidine in 0.05 M Tris (pH) saline containing 0.1% hydrogen peroxide. The sections were counter-stained with Mayer's hematoxylin.

K. Results

Antibody Reactivity:

The antiserum had a titer of 1:10,000 on A1/30 and CIF-A, and a titer of 1:1,000 on a partially purified CIF-A containing bone extract. The antibodies also reacted with TGF-beta from platelets, as expected, since the N-terminal sequence is identical.

The competitive ELISA method was used to determine if the antibodies detected by the ELISA were antigen-specific antibodies. In this experiment, the binding of an optimal dilution of antiserum (1:5,000) to 400 ng of peptide A1/30 bound to plastic was competed with variable amounts (1 to 100 ng) of soluble synthetic polypeptide. Antibody binding was competed in a linear dose-response type fashion and 100 ng of the soluble competitor competed binding by more than 80%. The linear titrations characteristics of the antibodies and linear and near complete competitions of binding suggest that the antibodies were antigen specific. The antibody specificity was also confirmed by immunoblotting methods in which the antibodies were immunoreactive with nonreduced CIF-A and with 2-mercaptoethanol-reduced CIF-A, as well as peptide A1/30. Having determined that the antibodies to peptide A1/30 were immunoreactive with CIF-A, they were used to determine if other molecular weight species of CIF-A were contained in crude bone extracts. High and low molecular weight bone extracts were prepared and the constituent proteins separated by gel electrophoresis. A silver stained gel and a duplicate immunoblot were prepared. The tests showed that antibodies to peptide A1/30 detected only a protein of the same molecular weight as CIF-A in both the high and low molecular weight bone extracts.

Cell Association and Tissue Distribution:

Osteocytes within the cancellous bone of the femur were specifically labeled by staining. In addition, there was intense staining of articular chondrocytes, particularly those cells in close association with the cartilage canals. Chondrocytes within the epiphyseal plate were not labeled by the antibodies.

Kidney tissue and platelets were examined. There was specific staining of the epithelial cells lining the calyxes, while surrounding stromal and parenchymal cells were not labeled by the anti-A1/30 antibodies. Bone marrow was also examined, and the platelet-producing megakaryocytes were specifically labeled by the antibodies. Some mononuclear bone marrow cells were also stained by the antibodies.

Staining was also carried out to determine if CIF-A might also be associated with centers of hematopoiesis and lymphopoiesis. There was intense cytoplasmic staining of clusters of hematopoietic stem cells in the fetal liver, while hepatocytes and stromal cells were not labeled. Hematopoietic stem cells in the bone marrow were specifically stained with the antibodies. The thymus was examined and specific staining of Hassall's corpuscle and some of the medullary thymocytes was observed. There was no specific staining of the less differentiated cortical thymocytes.

Other tissues were examined, including the thyroid, adrenal, and the submaxillary salivary gland, as well as the aorta. CIF-A was not detected in any of these tissue by the staining technique.

The localization of CIF-A/TGF-beta in centers of hematopoiesis (bone marrow and liver) and lymphopoiesis (thymus) indicates that the molecule may regulate red blood cell and/or lymphocyte differentiation in vivo. Accordingly, CIF may find use in therapy for indications associated with dysfunction or malfunction of hematopoiesis and/or lymphopoiesis such as congenital thymic aplasia, severe combined immunodeficiency, hereditary hemolytic anemia, and acquired hemolytic anemia. Such activity was also observed in Example 7 below.

EXAMPLE 4

(Activity of CIF on Lymphocytes)

A. Purification of Peripheral Blood Lymphocytes

Peripheral blood mononuclear cells were isolated from heparinized blood of healthy adult human donors in Ficoll-Hypaque density gradients. The red blood cell-free buffy coat was collected from the aqueous-ficoll interface. The monocytes were removed by incubating at 37° C. for 1 hr on tissue culture plastic in RPMI 1640 medium containing 10% fetal calf serum (FCS). The T lymphocytes were isolated from the non-adherent cells by rosetting with 0.25% sheep red blood cells (E-rosettes) for 2 hr at 37° C. The E-rosetted T lymphocytes were separated from the non-rosetted B lymphocytes by centrifugation through Ficoll-Hypaque for 30 to 40 min at 500$\times$g. The pellet was >95% E-rosetted cells. The sheep red blood cells were lysed with 0.83% ammonium chloride.

The nonrosetted B lymphocytes were collected from the ficoll-aqueous interface.

B. T Cell Mitogen Assay

T lymphocyte proliferation was evaluated using a mitogen microassay. The assay consisted of plating 0.2$\times 10^5$ T cells into 96-well microassay plates. The cells were cultured in RPMI 1640 medium supplemented with L-glutamine, penicillin streptomycin, and 10% FCS. The cultures were mitogen stimulated with Concanavalin-A (6.2 to 24 ug/ml). CIF-A or CIF-B was added to the microcultures between 0.01 to 40 ng/ml. The final culture volumes were adjusted to 250 ul, and the mixture was incubated for 5 days at 37° C. in a humidified incubator in a 5% $CO_2$ atmosphere. The cultures were pulsed with 1.0 uCi of $^3$H-thymidine (specific activity 25 Ci/mmole) 18 hr prior to harvesting with an automated cell harvester. Inhibition of $^3$H-thymidine incorporation by various concentrations of CIF-A or CIF-B was determined from triplicate cultures by the following formula:

$$\% \text{ inhibition} = 1 - \frac{\text{mitogen treated with } CIF \text{ (cpm)}}{\text{mitogen-treated control without } CIF \text{ (cpm)}} \times 100$$

C. B Cell Activation Assay

A lymphocyte culture was made by mixing $10^5$ T lymphocytes with 2.5$\times 10^5$ fresh autologous B lymphocytes. The cells were cultured at 37° C. in 5% $CO_2$ in 1 ml RPMI 1640 medium supplemented with L-glutamine, penicillin-streptomycin, and 10% FCS. The cultures were set up in 12×75 mm culture tubes. Pokeweed mitogen was added to cultures at a 1/100 dilution. To these cultures various concentrations ($1.9 \times 10^{-12}$ M, $1.9 \times 10^{-10}$ M, or $1.5 \times 10^{-9}$ M) of either CIF-A or CIF-B were added to the cultures. The cells were cultured for 7 days.

At the end of the culture period, the cell-free culture supernatants were assayed for IgM or IgG by a sandwich ELISA method. Flat-bottom polyvinyl chloride microtiter plates were incubated overnight at 4° C. with approximately 120 to 500 ug of affinity-purified goat anti-human IgM or IgG in phosphate-buffered saline (PBS). The plates were washed with PBS containing 0.05% Tween®-20 (PT buffer) in order to remove unbound antibody. The culture supernatants were diluted either 1/10 or 1/100 in PBS containing 0.05% Tween®-20 and 0.5% bovine serum albumen (PTB buffer). To generate a standard curve, various concentrations (2 to 10 ng) of purified human IgG or IgM were added to the appropriate wells. After 2 hr at room temperature, the plates were washed with PT buffer. One hundreds microliters of a 1/5,000 dilution of peroxidase-conjugated goat anti-human IgG or antihuman IgM were added to the wells. After a 1 hr incubation, the plates were washed with PT buffer, and 100 ul of freshly prepared substrate was added. The substrate consisted of ABTS, 0.03% (w/v), and 0.03% (v/v) hydrogen peroxide in 0.1 M citrate buffer (pH 4.0). Color was allowed to develop for 30 min and the optical density was determined at 414 nm. The concentration of IgG or IgM was calculated from a standard curve run simultaneously with the assays. Inhibition of IgG or IgM production by the B cells was calculated by comparing the CIF-A- or CIF-B-treated cultures to control cultures which were not treated with CIF. The following formula was used:

$$\frac{\% \text{ inhibition}}{\text{of antibody}} = 1 - \frac{\text{ng/ml } Ig \text{ (with } CIF)}{\text{ng/ml } Ig \text{ (without } CIF)} \times 100$$

Results

Figure 4:
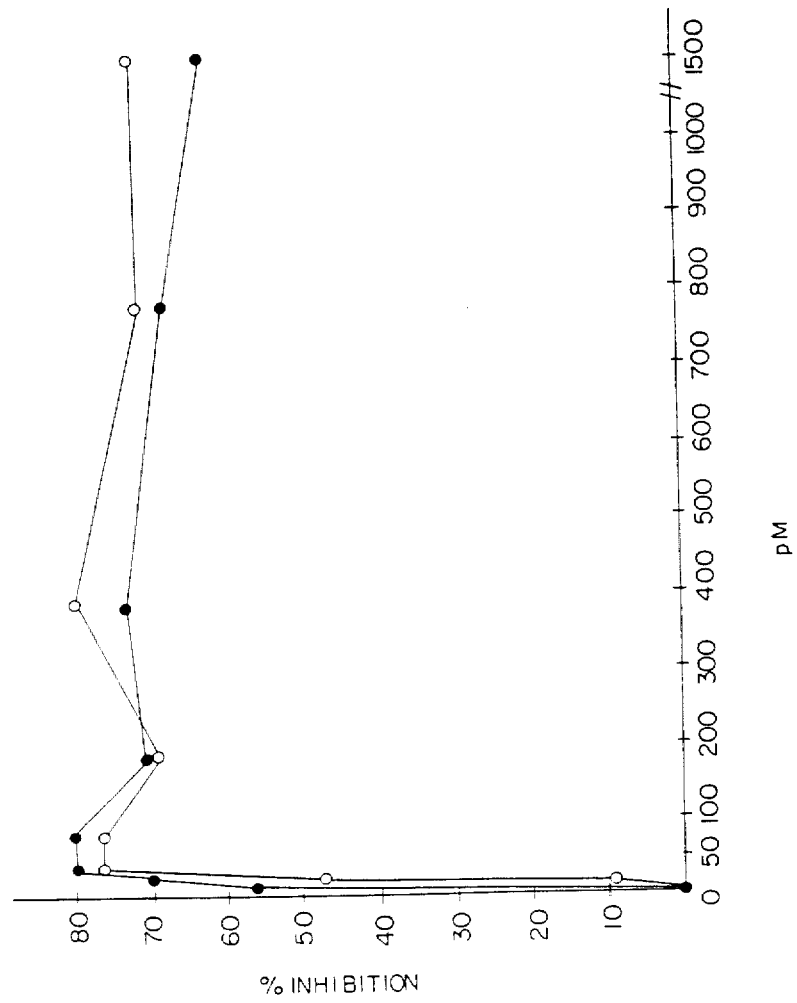
FIG. 4 is a graph of the results of the T cell proliferation assays described in Example 4 ( ¶ B).

The results of the T cell proliferation assays are plotted in FIG. 4. As seen in this figure, both CIF-A and CIF-B were found to have comparable activities upon T lymphocyte proliferation. $^3$H-thymidine incorporation was inhibited by 78% to 80% by approximately $38 \times 10^-$ M CIF-A or CIF-B. The half-maximal activity for CIF-A was less than $1 \times 10^{-12}$ M. The half-maximal activity for CIF-B was estimated to be approximately $1.9 \times 10^{-12}$ M. These results show clearly that both CIFs are potent inhibitors of human T lymphocyte proliferation.

The results of the B cell activation assay are summarized in Table 2 below. The data presented represent the mean ± SD for the three experiments.

TABLE 2

| CIF Concent. | IgM (ng/ml) | Inhibition (%) | IgG (ng/ml) | Inhibition (%) |
|---|---|---|---|---|
| 0 | 364.9 ± 202.5 | — | 66.0 ± 12.2 | — |
| CIF-A | | | | |
| $1.9 \times 10^{-12}$ M | 244.5 ± 302.8 | 33.0 | 56.4 ± 41.2 | 16.0 |
| $1.9 \times 10^{-10}$ M | 0 ± 0 | 100.0 | 29.6 ± 16.6 | 56.0 |
| $1.5 \times 10^{-9}$ M | 0 ± 0 | 100.0 | 31.1 ± 15.6 | 54.0 |
| CIF-B | | | | |
| $1.9 \times 10^{-12}$ M | 292.6 ± 368.5 | 20.0 | 66.2 ± 10.4 | 1.0 |
| $1.9 \times 10^{-12}$ M | 0 ± 0 | 100.0 | 31.0 ± 12.2 | 54.0 |

TABLE 2-continued

| CIF Concent. | IgM (ng/ml) | Inhibition (%) | IgG (ng/ml) | Inhibition (%) |
|---|---|---|---|---|
| $1.5 \times 10^{-9}$ M | 0 ± 0 | 100.0 | 7.3 ± 6.0 | 89.0 |

As shown in Table 2, CIF-A at $1.9 \times 10^{-12}$ M reduced the amount of IgM produced by 33% and IgG by 16% when compared with the nontreated control culture. There was complete inhibition of IgM production in cultures containing either $1.9 \times 10^{-10}$ M or $1.5 \times 10^{-9}$ M concentrations of CIF-A. Similar concentrations of CIF-A resulted in a 54% to 56% inhibition of IgG production.

CIF-B was found to be comparable to CIF-A. As seen in Table 2, cultures containing $1.9 \times 10^{-10}$ M concentrations of CIF-B contained no IgM and only 54% of the IgG when compared with the untreated control cultures. Cultures treated with $1.5 \times 10^{-9}$ M concentrations of CIF-B contained no measurable IgM and very little (89% inhibition) or no IgG. These results show that both CIF-A and CIF-B are extremely potent inhibitors of antibody production by plasma cells.

These in vitro T cell proliferation and B cell activation experiments suggest that lymphocyte regulation may be one mechanism involved in the in vivo lymphohistiocytic anti-inflammatory activity of CIF observed previously. The results of these tests confirm the work reported by Kehrl, J. H., et al, Clinical Research (1985) 33:610A.

EXAMPLE 5

(CIF in Rodent Arthritis Model)

Experimental collagen-induced arthritis (ECIA) can be induced in rats by intradermal injection of native type II collagen (bovine or rat) emulsified in incomplete Freund's adjuvant. The inbred Lewis rat strain, LEW (RT1$^1$), has been shown to develop peripheral polyarthritis within 14 to 30 days following immunization. Joint and ear cartilage develop a diffuse mononuclear cell infiltrate. Sensitized rats respond to intradermal skin test challenge and develop circulating antibodies to native type II collagen.

Twelve LEW rats (12–15 weeks old) are divided into three groups of four animals each. Groups I and II are sensitized to type II bovine collagen by intradermal injection of bovine type II in complete Freund's adjuvant at 2.5 ml/kg weight. Group III serves as a nonsensitized control.

Ankle measurements and subjective grading (0 to +4) of arthritis based on the degree of inflammation and swelling of digits, feet and ankles are made prior to sensitization and regularly throughout the test. Rats in Group I exhibiting a significant inflammatory response are treated by injection of CIF (500 ng in 0.05 ml sterile PBS) directly into the joint on days 1, 3, 5, and 7 following the observed response. Rats of Group II showing such a response are treated similarly by injection of PBS without CIF.

Sera are collected from the rats pre-treatment and post-treatment and assayed for antibodies to type II collagen using an ELISA. The rats are given an intradermal skin test challenge at 3 days prior to sacrifice using 50 ug of type II collagen in the abdomen. Erythema and induration are measured at 24, 48, and 72 hr post challenge. At 72 hr the challenge site is biopsied and examined histologically.

Rats are sacrificed 5 to 7 days after the final injection, exsanguinated, and their paws fixed in 10% neutral formalin for histologic examination.

The results of these tests show that treatment with CIF reduces inflammation significantly compared to the nontreated control group. The CIF-treated groups exhibit a reduced response to a skin test challenge of type II collagen when compared with the nontreated control group. Further, the treated group has significantly reduced antibody titers to type II collagen. These results suggest that administration of CIF into the affected joints not only controls the inflammation locally, but acts as a systemic immunosuppressive agent for the treatment of arthritis.

EXAMPLE 6

(Suppression of Skin Graft Rejection)

Graft rejection is mediated through the generation of an immune-mediated inflammatory response to histocompatibility antigens on the transplanted tissue. Transplant rejection can be prevented by treating the transplant recipient with agents which suppress the generation of the immune response. To demonstrate the efficacy of CIF as an immunosuppressive agent for use in transplantation, two transplantation models were used. The first model demonstrated that CIF can be delivered locally into a transplanted organ (e.g., skin graft) and thereby promote engraftment. The second model involves systemically administering CIF to prevent heart transplant rejection (Example 7).

The ability of CIFs to suppress inflammation accompanying grafts or transplants was examined using full-thickness skin grafts between non-histocompatible mice.

Strain C3H mice (H-$2^k$) were shaved and swabbed with antiseptic. Next, 2 cm×2 cm full-thickness skin grafts were removed using a microtome, and the undersurface scraped with a rounded-edged scalpel to remove subcutaneous fat. If necessary, the skin can be cut to any desired size or shape. The graft was then soaked in a saline solution containing CIF-A (50 ug/ml) and 1% mouse serum albumin (MSA). Control grafts were soaked in saline with 1% MSA. The grafts were soaked for 30 minutes at 25° C.).

BALB/c mice (H-$2^d$) were used as graft recipients. The graft sites were prepared by excising a shaved 2 cm×2 cm full-thickness section of skin from the back of each mouse, and cleaning and debriding the wound bed. A soaked C3H skin section was placed in each graft site, and overlaid with a 2×2 cm piece of Owen's cloth, a 2×2 cm piece of Telfa nonadhesive pad, and a layer of tape to hold the pads in place. Subjects were observed daily. Graft viability was assessed at 10 days by histological examination of the grafted skin. The results are presented below:

| Treatment | No. of mice | Graft Survival |
|---|---|---|
| Control | 10 | 10% |
| CIF-A | 9 | 77% |

Grafts which were pretreated by perfusion with CIF-A at 50 ug/ml exhibited evidence of a viable epithelial layer, intact hair follicles, neovascularization of the graft, and extensive granulation tissue within the wound bed. Few polymorphonuclear cells and mononuclear cells were found within the graft or wound bed, indicating suppression of inflammation and graft rejection.

The control skin grafts, pretreated by perfusion with vehicle (1% MSA in saline) exhibited no evidence of viable epithelium or hair follicles, and a lack of neovascularization. The graft bed contained a mixed inflammatory infiltrate which extended into the allograft, indicating that the graft had been rejected by the host.

EXAMPLE 7

(CIF In Cardiac Allograft Model)

The following experiment demonstrates the use of CIFs administered systemically for treatment of subjects with solid organ transplants, such as heart or kidney transplants. The model used is a particularly severe test for an anti-inflammatory agent, as it requires the suppression of inflammation (in this case, graft rejection) due to the presence of tissue with non-matched MHC antigens. The systemic administration also afforded an opportunity to observe the hematologic effects of CIF administration. The effective amount for systemic administration is currently believed to be within the range of about 50 ug to about 5 mg/Kg body weight.

Neonatal hearts were obtained from 1-2 day old Balb/C mice (H-$2^d$). A receiving pocket was surgically prepared in the ear pinnae of C3H/HeN mice (H-$2^k$), and the heart inserted using a trochar.

Transplant recipients were treated daily, beginning one day before implantation and continuing for 14 days after implantation. Treatments were by subcutaneous injection of one of the following preparations: 1% MSA in saline (vehicle control); 50 ug/mouse/day CIF-A with 1% MSA in saline (experimental); and 0.6 mg/mouse/day cyclosporin-A (CyA) in olive oil (positive control).

Transplanted animals were sacrificed at day 14. All graft sites were examined histologically for graft viability and extent and type of inflammatory infiltrate. One-way mixed lymphocyte reactions and mitogen-induced lymphocyte proliferation experiments were conducted to determine recipient sensitivity to donor antigens.

Results:

The vehicle control group exhibited general graft rejection. Histologic examination revealed a vigorous mixed inflammatory infiltrate throughout the transplant, with no evidence of viable myocardiocytes. The experimental group (CIF-A) and positive control (CyA) exhibited reduced levels of inflammatory infiltrate, with viable myocardiocytes present (although spontaneous contractile activity had ceased in the experimental group). This indicates graft acceptance in the CIF-A and CyA groups.

The mixed-lymphocyte reactions were conducted to determine if the recipient animals had become sensitized to the donor MHC antigens. Briefly, the spleens were removed from the transplant recipient mice (C3H/HeN), and the cells suspended at 5×$10^6$ cells/ml in complete culture medium. Fresh donor (Balb/C) spleen cells (1×$10^7$) were treated with mitomycin C (25 ug) for 20 minutes, then washed to remove excess mitomycin C, and resuspended at 5×$10^6$ cells/ml. As controls, 0.1 ml of mitomycin C-treated responder cells (C3H/HeN) were added to 0.1 ml untreated responder cells in triplicate on 96-well microtiter plates. Experimental cultures contained 0.1 ml nontreated responder cells with 0.1 ml treated stimulator (Balb/c) cells. The cultures were incubated for 5 days at 37° C. under 5% $CO_2$. During the final 24 hours, the cell cultures were pulsed with 1 uCi of $^3$H-thymidine, then harvested using a cell harvester. The amount of incorporated $^3$H-thymidine was determined using standard liquid scintillation techniques, and the results expressed as the stimulation index (SI, mean±sem):

$$SI = \frac{\text{experimental (cpm)}}{\text{control (cpm)}} \times 100$$

The mean results were as follows:

| Group | Stimulation index | Reduction from Control (%) |
|---|---|---|
| Control | 10.8 ± 0.7 | 0 |
| CIF-A | 7.7 ± 1.2** | 29 |
| CyA | 3.6 ± 0.7* | 67 |

*Significantly different from control at p = 0.05 by Dunnett's T test.
**Approaching significance.

The data show a vigorous lymphocyte response to alloantigen in the control group, indicating high sensitivity. The CIF-A and CyA groups exhibit marked reductions in lymphocyte response, indicating the CIF-A and CyA treated animals had a depressed immune response to the donor MHC antigens.

Lymphocyte proliferation was testing using the mitogens concanavalin-A (Con-A), pokeweed mitogen (PWM), and lipopolysaccharide (LPS). To assay the mitogen-induced proliferation, the spleen and lymph nodes of recipient mice were suspended in complete culture media at $2 \times 10^6$ cells/ml, and plated at $2 \times 10^5$ cells in 96-well microtiter plates. The cells were stimulated with either ConA (2.5 ug/ml), PWM (10 ug/ml), or LPS (100 ug/ml) for 72 hours at 37° C. under 5% $CO_2$. The cells were pulsed with 1 uCi $^3$H-thymidine for the final 24 hours of culture, and uptake determined by liquid scintillation. Stimulation was calculated by $$SI = \frac{\text{uptake with mitogen (cpm)}}{\text{uptake without mitogen (cpm)}} \times 100$$

The results were as follows:

|  | ConA | PWM | LPS |
|---|---|---|---|
| Control | 281.9 | 8.3 | 2.0 |
| CIF-A | 1.9* | 1.4* | 1.2* |
| CyA | 1.3* | 1.3* | 1.4 |

*Significantly different from control at p = 0.05 by Dunnett's T test. Data are expressed as stimulation index.

These results demonstrate that CIF-A and CyA treated animals were completely immunosuppressed, and that the immunosuppression involved T cell and B cell populations.

Hematological studies demonstrated substantially decreased platelet counts in CIF-A-treated animals ($6 \times 10^4$/mm$^3$ for CIF-A vs. $1-2 \times 10^6$/mm$^3$ for control and CyA groups). Erythrocyte packed cell volume (PCV) was also decreased by about 50% compared to control and CyA groups. These observations support the utility of CIF-A in treating hematological disorders, for example, polycythemia, thrombocytosis, splenomegaly, and the like.

EXAMPLE 8

(Myelosuppression using CIF)

The allograft experiments set forth above demonstrate that CIFs exhibit potent immunosuppressive activity in vivo, and that these factors can be administered both locally and systemically to prevent transplant rejection.

Additional experiments were conducted in order to better characterize the immunosuppressive actions of CIF and to determine the effect of CIF upon the generation and development of immune and other inflammatory cells. In these experiments, mice were treated by subcutaneous injection of CIF or the vehicle (phosphate-buffered saline containing 1% MSA).

CIF was administered at 50 ug/day/mouse daily for 14 days. CyA was administered at 0.6 mg/day/mouse (in olive oil) for 14 days by subcutaneous injection as a positive control. All assessments were made on day 15.

Hematologic Changes:

Peripheral blood was obtained immediately prior to treatment and at sacrifice, and hematologic changes determined by packed cell volume (PCV), differential cell counts, and hemoglobin. The results are depicted in FIGS. 5–7.

Figure 5A:
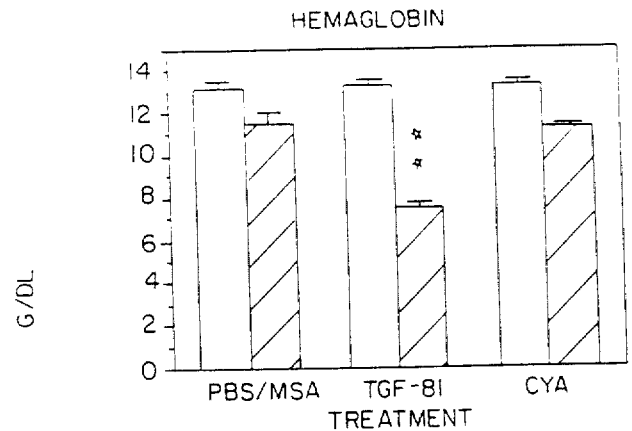
FIG. 5A depicts hemoglobin in grams per 100 mL.
Figure 5B:
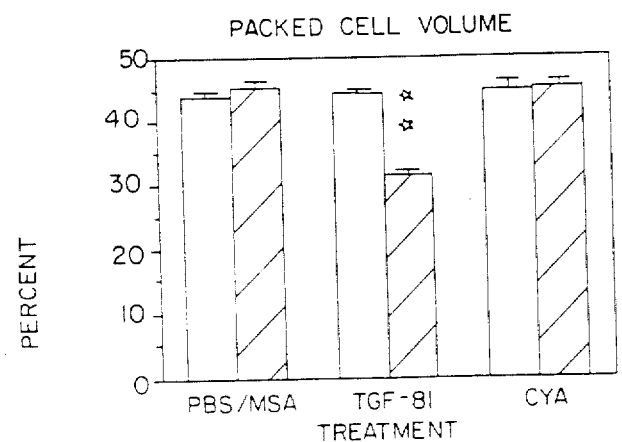
FIG. 5B shows packed cell volume in percent.
Figure 5C:
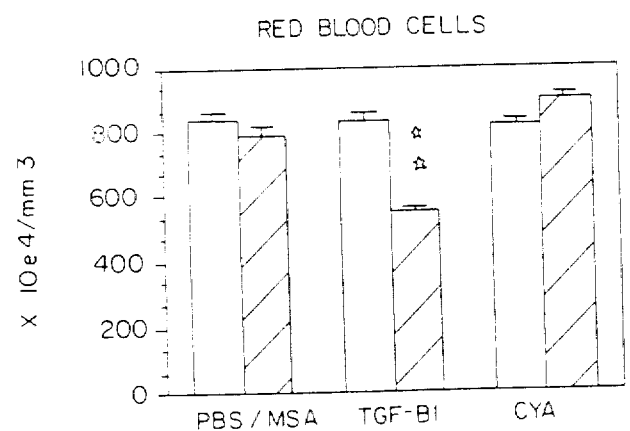
FIG. 5C shows red blood cell count in number ($\times 10^4$) per cubic mm.

FIG. 5 shows that the peripheral red blood cell counts were significantly depressed (30–40%) in the CIF-A treated animals. This result was consistent with all the red blood cell parameters, including hemoglobin assessment (FIG. 5A), packed cell volume (FIG. 5B), and total circulating red blood cells (FIG. 5C).

Figure 6A:
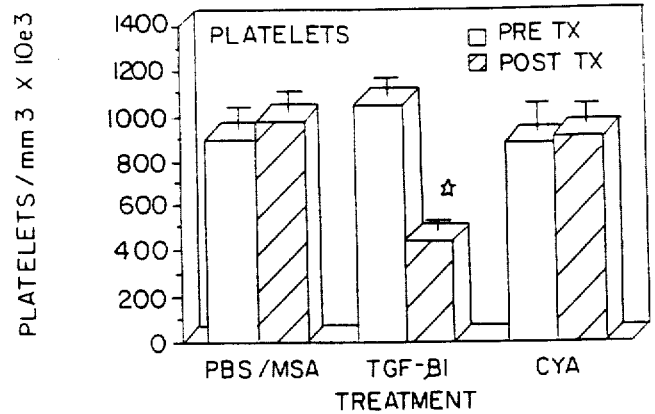
FIG. 6A shows the platelet count in number ($\times 10^3$) per $mm^3$.
Figure 7A:
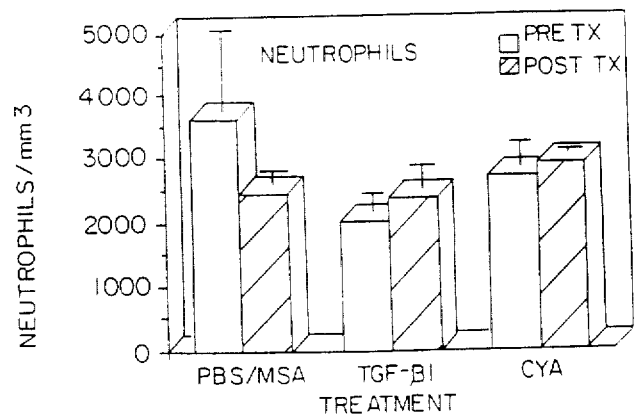
FIG. 7A shows the neutrophil count in cells per $mm^3$.
Figure 7B:
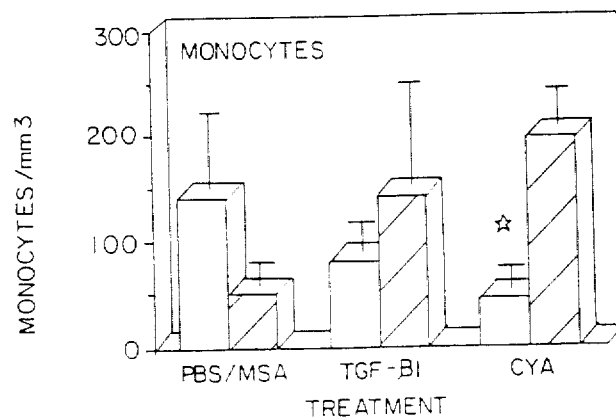
FIG. 7B shows the monocyte count in cells per $mm^3$.
Figure 7C:
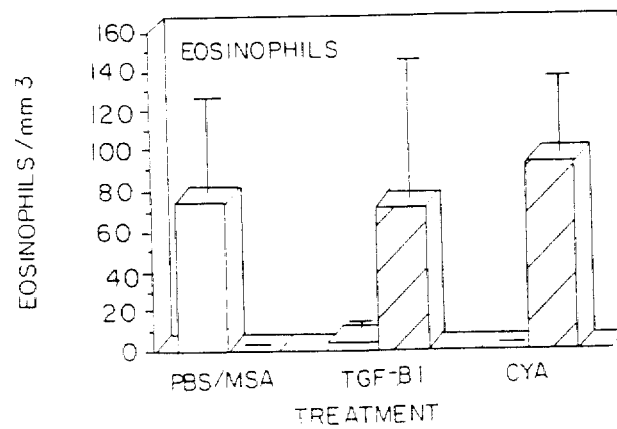
FIG. 7C shows the eosinophil count in cells per $mm^3$.

Platelet cell counts were also significantly depressed in the CIF-A treated animals (FIG. 6A).

Figure 6B:
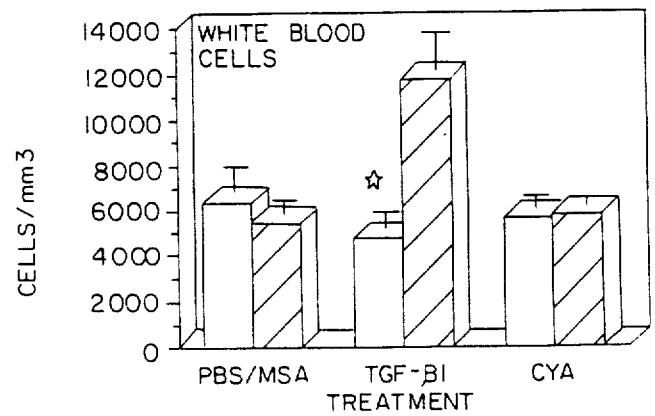
FIG. 6B shows the white blood cell count in cells/$mm^3$.
Figure 6C:
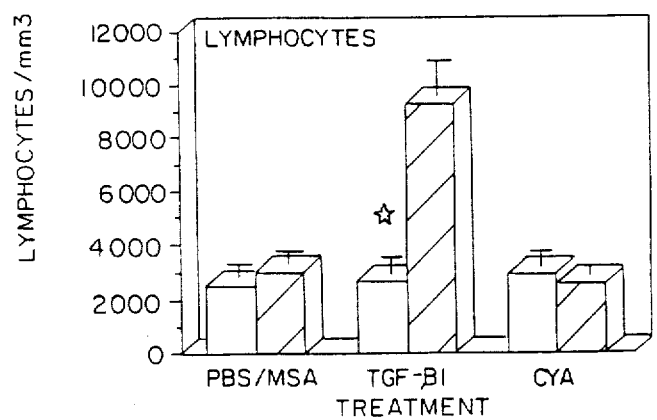
FIG. 6C shows the lymphocyte count in cells/$mm^3$.

Differential white cell counts were determined and the results illustrated in FIGS. 6B and 6C, and FIGS. 7A–C. As seen in FIGS. 6B–C, the total white cell counts were significantly increased in the CIF-A treated animals. These elevated white blood cells were found to be specifically of the mononuclear or lymphocyte type (FIG. 6C). The circulating neutrophil (FIG. 7A) and eosinophil (FIG. 7C) cell counts did not appear to be significantly altered by CIF-A treatment. These results suggest that the suppressive effects of CIF-A are selective, in that the factor can suppress the generation of some hematopoietic and lymphopoietic cell populations while sparing or permitting the development of other cell populations.

The hematological changes were further confirmed by histologic examination of the immune and hematopoietic organs.

The most striking difference between spleens from control and CyA treated animal, and those from mice treated with CIF-A, was in the intense proliferation of cells of the granuloid lineage within the red pulp zones of the spleens. Juvenile neutrophillic metamyelocytes, with donut or band nuclear configurations filled the sinusoids and subcapsular sites in all specimens treated for 14 days with CIF-A. Occasional eosinophilic colonies were also distinguished. This splenic granulocytopoiesis was not of an inflammatory nature, but rather a hematopoietic induction of normal granulopoiesis by CIF-A. The red pulp areas of the spleen did show evidence of diminished numbers of mature red blood cells. However, splenic erythropoiesis within the red pulp was also elevated in the CIF-A treated group, with the proerythroblast and basophilic erythroblast stages heavily represented. These results suggest that CIF-A is suppressing the terminal differentiation of cells of the myeloid and erythroid lineages, and is consistent with the hematologic changes.

Histological changes observed in the spleen of CIF-A treated mice were also observed in the bone marrow. CIF-A treated animals exhibited a reduction in the mature red blood cell population, although less differentiated red blood cell precursor cells were present. Again, this suggests that CIF-A has myelosuppressive effects on the bone marrow as well as progenitor cell populations in the spleen.

These results indicate that CIFs are useful for treating hematologic disorders or dysfunctions involving a hyperproliferative or an over-production of hematopoietic cell populations. The factors, therefore, have therapeutic utility for treating polycythemia, thromobocytosis, splenomegaly, and the other non-leukemic disorders.

Modifications of the modes for carrying out the invention that are obvious to those of ordinary skill in the fields of protein chemistry, pharmaceutical formulation, reconstructive surgery, and related fields are intended to be within the scope of the following claims.

We claim:

1. A method of treating a subject for inflammation associated with a graft or transplant, which method comprises:
   administering an anti-inflammatorily effective amount of a cartilage inducing factor to the subject having a graft or transplant, wherein the cartilage inducing factor is a homodimer whose chains each have or are substantially homologous to the following partial N-terminal amino acid sequence:
   (a) Ala-Leu-Asp-Thr-Asn-Tyr-Cys-Phe-Ser-Ser-Thr-Glu-Lys-Asn-Cys-Cys-Val-Arg-Gln-Leu-Tyr-Ile-Asp-Phe-Arg-Lys-Asp-Ley-Gly-Trp-, or
   (b) Ala-Leu-Asp-Ala-Ala-Tyr-Cys-Phe-Arg-Asn-Val-Gln-Asp-Asn-Cys-Cys-Ley-Arg-Pro-Leu-Try-Ile-Asp-Phe-Lys-Arg-Asp-Leu-Gly-Trp-.

2. The method of claim 1 wherein the cartilage inducing factor is a homodimer whose chains each have the amino acid sequence shown in FIG. 1.

3. The method of claim 1 wherein the cartilage inducing factor is substantially free of activating agent or cofactor.

4. The method of claim 1 wherein the cartilage inducing factor is administered by perfusing the graft or transplant tissue prior to implantation in the subject.

5. The method of claim 1 wherein the cartilage inducing factor is administered systemically.

6. The method of claim 1 wherein the cartilage inducing factor is administered by subcutaneous injection.

7. A method of treating a subject for an indication associated with hyperproliferation of erythrocytes or platelets comprising administering an effective amount of a cartilage inducing factor to the subject, wherein the cartilage inducing factor is a homodimer whose chains each have or are substantially homologous to the following partial N-terminal amino acid sequence:
   (a) Ala-Leu-Asp-Thr-Asn-Tyr-Cys-Phe-Ser-Ser-Thr-Glu-Lys-Asn-Cys-Cys-Val-Arg-Gln-Leu-Tyr-Ile-Asp-Phe-Arg-Lys-Asp-Leu-Gly-Trp-, or
   (b) Ala-Ley-Asp-Ala-Ala-Tyr-Cys-Phe-Arg-Asn-Val-Gln-Asp-Asn-Cys-Cys-Leu-Arg-Pro-Leu-Tyr-Ile-Asp-Phe-Lys-Arg-Asp-Ley-Gly-Trp-.

8. The method of claim 7 wherein said indication is selected from the group consisting of polycythemia, thrombocytosis, and splenomegaly.

* * * * *

UNITED STATES PATENT AND TRADEMARK OFFICE
CERTIFICATE OF CORRECTION

PATENT NO. : 4,971,952

DATED : November 20, 1990

INVENTOR(S) : Hanne Bentz, et al.

It is certified that error appears in the above-identified patent and that said Letters Patent is hereby corrected as shown below:

The sheets of drawings consisting of figures 4-7, should be added as shown on the attached pages.

On the title page, "8 claims, 3 Drawing Sheets" should read-- 8 Claims, 7 Drawing Sheets--.

Signed and Sealed this

Fifteenth Day of June, 1993

Attest:

MICHAEL K. KIRK

Attesting Officer

Acting Commissioner of Patents and Trademarks